US009389224B2

(12) United States Patent
Budd et al.

(10) Patent No.: US 9,389,224 B2
(45) Date of Patent: Jul. 12, 2016

(54) COATED BEADS

(75) Inventors: Roger Budd, Birmingham (GB); David Taylor, Brimingham (GB)

(73) Assignee: The Binding Site Group Limited, Birmingham, West Midlands (GB)

( * ) Notice: Subject to any disclaimer, the term of this patent is extended or adjusted under 35 U.S.C. 154(b) by 233 days.

(21) Appl. No.: 13/881,237

(22) PCT Filed: Oct. 26, 2011

(86) PCT No.: PCT/GB2011/052079
§ 371 (c)(1),
(2), (4) Date: Jul. 1, 2013

(87) PCT Pub. No.: WO2012/056233
PCT Pub. Date: May 3, 2012

(65) Prior Publication Data
US 2014/0147933 A1     May 29, 2014

(30) Foreign Application Priority Data

Oct. 27, 2010   (GB) .................................. 1018096.6

(51) Int. Cl.
*G01N 33/543*     (2006.01)
*A61K 9/50*       (2006.01)
*G01N 33/53*      (2006.01)

(52) U.S. Cl.
CPC ........ *G01N 33/54313* (2013.01); *A61K 9/5078* (2013.01); *G01N 33/5306* (2013.01); *G01N 33/54393* (2013.01)

(58) Field of Classification Search
CPC ............ A61K 9/5078; G01N 33/5306; G01N 33/54393; G01N 33/54313

USPC .......................................................... 436/518
See application file for complete search history.

(56) References Cited

U.S. PATENT DOCUMENTS

| 4,811,741 | A  | * | 3/1989 | Shell et al. .................... 600/504 |
| 6,183,952 | B1 | * | 2/2001 | Billing-Medel et al. ..... 435/6.14 |
| 2003/0119073 | A1 | * | 6/2003 | Quirk et al. .................... 435/7.4 |
| 2003/0148362 | A1 |   | 8/2003 | Luka |

(Continued)

FOREIGN PATENT DOCUMENTS

| CN | 101762690 | 6/2010 |
| EP | 1069433   | 1/2001 |

(Continued)

OTHER PUBLICATIONS

PCT Search Report and Written Opinion for PCT/GB2011/052079, completed Feb. 6, 2012.

(Continued)

*Primary Examiner* — Mark Shibuya
*Assistant Examiner* — Pensee Do
(74) *Attorney, Agent, or Firm* — Barnes & Thornburg LLP

(57) ABSTRACT

The invention relates to a method of coating beads with a biological molecule comprising: (i) coating a plurality of beads with the biological molecule; (ii) mixing the coated beads with a liquid stabilizing and/or blocking agent (iii) dispersing the coated beads still substantially surrounded by a liquid phase comprising the liquid stabilizing and/or blocking agent across a surface that is at least partially liquid permeable; (iv) drying the beads on the surface to substantially remove the liquid phase; and (v) removing the dried beads from the surface.

11 Claims, 3 Drawing Sheets

(56) References Cited

U.S. PATENT DOCUMENTS

| | | | |
|---|---|---|---|
| 2003/0165970 A1* | 9/2003 | Hu | 435/6 |
| 2004/0009529 A1* | 1/2004 | Weimer et al. | 435/7.1 |

FOREIGN PATENT DOCUMENTS

| | | |
|---|---|---|
| WO | WO03056301 | 7/2003 |
| WO | WO03057852 | 7/2003 |
| WO | WO03066906 | 8/2003 |
| WO | 2008/124936 | 10/2008 |

OTHER PUBLICATIONS

United Kingdom Search Report for GB1018096.6, completed Mar. 10, 2011.

Crowther et al., *The Elisa Theory and Practice*. Humana Press, ISBN:0-89603-279-5 (1995; Book reference not submitted herewith, but may be submitted upon Examiner's request).

Park, J-W et al., Comparison of stabilizing effect of stabilizers for immobilized antibodies on QCM immunosensors, Sensors and Actuators B, 91:158-162 (2003).

Wang, W., Protein aggregation and its inhibition in biopharmaceutics, Intl. Jour. of Pharmaceutics, 289:1-30 (2005).

Sali, A. et al., How does a protein fold?, Nature, 369:248-251 (1994).

Leung, W. et al., One-step quantitative cortisol dipstick with proportional reading, Jour. of Immunological Methods, 281:109-118 (2003).

Asakura, T. et al., Stabilizing Effect of Various Organic Solvents on Protein, J. Bio Chem., 253(18):6423-6425 (1978).

Burley, S. and G. Petsko, Aromatic-Aromatic Interaction: A Mechanism of Protein Structure Stabilization, Science, 229:23-28 (1985).

Maish, M., http:/www.sparknotes.com/health/aminoacids (2005; 2015 Webpage submitted).

Wang, W., Instability, stabilization, and formulation of liquid protein pharmaceuticals, Intl. Jour. of Pharmaceutics, 185:129-188 (1999).

Wild D.G. et al., *The Immunoassay Handbook*, Elsevier, ISBN: 0-08-044526-8 (2005; Book reference not submitted herewith, but may be submitted upon Examiner's request).

Engvall, E. and P. Perlmann, Enzyme-linked Immunosorbent Assay (ELISA). Quantitative Assay of Immunoglobulin G, Immunochemistry, 8:871-873 (1971).

Klotz, I., Protein Conformation: Autoplastic and Alloplastic Effects, Archives Biochemistry & Biophysics, 116:92-96 (1966).

Kanehisa, M. and T. Tsong, Local hydrophobicity stabilizes secondary structures in proteins, Biopolymers, 19:1617-1628 (1980).

Torchilin, V.P. and K. Martinek, Enzyme stabilization without carriers, Enzyme and Microbiological Technology, 1:74-82 (1979).

* cited by examiner

COATED BEADS

CROSS REFERENCE TO RELATED APPLICATIONS

This application is a U.S. national counterpart application of International Application No. PCT/GB2011/052079 filed Oct. 26, 2011, which claims priority to G.B. Patent Application No. 1018096.6, filed Oct. 27, 2010. The entire disclosures of PCT/GB2011/052079 and G.B. Patent Application No. 1018096.6 are hereby incorporated by reference.

The invention relates to methods of coating beads with a biological molecule and to beads coated with biological molecules.

Diagnostic immunoassays, such as enzyme linked immunosorbent assay (ELISA)[1,2] are widely used in research and industry and are important and sensitive analytical techniques for numerous; diagnostic, clinical, biochemical, environmental and genetic applications[3,4]. These assays use proteins (e.g., antigens and antibodies) immobilized onto a solid support together with detection proteins labelled with chromogenic, fluorescent, radioactive and chemiluminescent molecules and/or conjugated with other biomolecules including enzymes that act as enhancers or substrates for the reporter agent.

In order to successfully manufacture immunoassay solid supports with an extended shelf life greater than a few days/weeks, it is necessary to preserve the physical integrity of the immobilised target antigen or antibody. This is influenced by a number of external factors, including; moisture, temperature, pH, salt, metal ions, and other contaminants. Proteins for example are large flexible molecules with functional three-dimensional structures[5]. The spatial arrangements of amino acids in the catalytic and/or binding site regions are dependent upon the interaction of amino acids with one another, and other surrounding molecules[6-8]. It is the unique structure of proteins, along with the local environmental conditions that determine protein stability. The nature of the bound and other molecules in this system influences the degree of non-specific binding in an immunoassay. Thus all components used at this initial level must be rigorously evaluated to ensure there is no non-specific binding. In addition other components used within the assay, including sample diluents, wash buffers and conjugated proteins need to be likewise assessed. The addition of certain proteins and or detergents can reduce unwanted non-specific binding significantly.

Under certain conditions proteins will unfold into non-functional forms. Exposure to temperatures above a certain limit will cause thermally unstable proteins to unfold and become denatured. High concentrations of solute, extremes of pH, mechanical forces and the presence of other chemical agents are potential inactivators. A fully denatured protein lacks both tertiary and secondary structure and as a consequence loses or reduces its ability to bind or be bound by corresponding reactants within the immunoassay.

The primary protein structure consists of a linear sequence of specific amino acids. Complex structures are produced by folding to form secondary, tertiary and ultimately quaternary structures as polypeptide chains are formed and interact with each other[9]. The amino acid building blocks can be hydrophilic and hydrophobic the more hydrophobic amino acids cluster in the interior of the globular molecule, whereas the hydrophilic or polar amino acids are concentrated at the exterior, this arrangement results in spontaneous folding in solution[10,11]. In addition electrostatic interactions, hydrogen bonding, and Van der Waals forces are all involved in this folding process. Correct folding ensures appropriate biological activity of the protein, and proteins in their native state are the most stable[12,13].

It is therefore logical that proteins stored and used in an environment that stabilizes and preserves their native structure will retain their function and activity. Proteins stored in solution generally have a shorter shelf-life than dried forms due to their continued interaction with surrounding molecules in their hydrated state. Drying and freezing minimizes or halts this interaction, provided the correct stabilising conditions are utilised otherwise denaturisation will still occur. In solution generally proteins are more stable at high concentrations and low temperatures. At low temperatures, protein interactions have less kinetic energy. At higher protein concentrations less protein activity is lost by the adsorption to container surfaces and through the action of enzymes and inactivation by other low levels contaminants. Typically any proteolytic enzymes present in the protein source (e.g., hydrolases and oxidases) are removed, thus water used in coating and stabilising solutions will usually be of high quality.

Many companies that manufacture immunoassays of this type have their own proprietary methods for coating and stabilising solid supports and as one may expect some perform better than others, general guidance is given in books published on general ELISA principles and applications[1,2]. Antibodies and antigens are typically bound to the inside of wells of microwell plates and incubated for approximately 12 hours at room temperature or 4° C., at which stage excess unbound material is aspirated and a block/stabiliser is added, binding is typically by, but not restricted to electrostatic forces. Intervening wash steps can be added as required. A block stabiliser is incubated nominally for 30 minutes at room temperature, to allow the reactants to both bind to any unbound sites on the solid support, and also integrate with the bound antibody or antigen. In the next step excess block/stabiliser is removed, such that a physical film of the reagent covers the bound protein. The next step is designed to dry the reactants on the solid support whist maintaining their integrity. There are two methods typically used to achieve this, firstly by incubation in a conventional laboratory incubator at 37° C. for 12-24 hours, or alternatively vacuum drying for between 1 and 24 hours depending on the volume of material to be dried. In our experience the latter offers the significant advantage of minimal initial loss of activity and longer term stability.

Vacuum drying is a process in which materials are dried in a reduced pressure environment, reducing the amount of heat needed for rapid drying, in a vacuum drier the temperature is not elevated and drying is faster. This technique allows us achieve very high level of dryness, enabling solid support stabilities in excess of two years at elevated temperatures (37° C.). The combination of vacuum drying and the stabilisation reagents we employ retain the integrity of the protein without damaging it with heat.

There are a number of proprietary blocking and stabilising solutions ready to use products on the market, that have been reported to effectively stabilise solid supports, including SurModics Inc. StabilCoat® and StabilGuard®[14] and also sucrose and/or lactose with and without bovine serum albumin (BSA), in addition other protein blockers are commonly used including gelatine and reconstituted skimmed milk powder 0.1-3% w/v.

An alternative solid phase support has recently become available consisting of large beads such as polystyrene bead (2 mm) diameter range could be wider 0.5-5 mm. These are coated with antibody or antigen, blocked and stabilised, dried and inserted into a microplate well composed of a biologically inert plastic e.g. polypropylene, such that no addition blocking of this component for non-specific binding is required. Initial application of generally known methods, resulted in dried clumps of beads, it is crucial to this application to obtain beads that are uniformly coated, do not form solid clusters and are free flowing.

The Applicant has identified a way of creating uniformly coated beads that do not form solid clusters and are free flowing.

Accordingly the method provides:

A method of coating beads with a biological module comprising:
(i) coating a plurality of beads with the biological molecule;
(ii) mixing the coated beads with a liquid stabilising and/or blocking agent
(iii) dispersing the coated beads still substantially surrounded by a liquid phase comprising the liquid stabilising and/or blocking agent across a surface that is at least partially liquid permeable;
(iv) drying the beads on the surface to substantially remove the liquid phase; and optionally removing the dried beads from the surface.

Biological molecules may be for example, a nucleic acid (such as DNA or RNA), lipopolysaccaride, polysaccharide, protein or peptides. Typically, the biological molecule is a protein or peptide.

Preferably the biological molecule is an antibody or fragment therefore capable of specifically binding an antigen, or an antibody. The antigen may be a biological molecule, such as a protein or peptide, nucleic acid, lipopolysaccharide or saccharide.

The stabilising and/or blocking agent is liquid when mixed with the coated beads. Typically, excess liquid stabilising and/or blocking agent is removed. The coated beads are then still substantially surrounded by a liquid phase comprising the liquid stabilising and/or blocking agent. The amount of liquid retained surrounding the coated bead is typically approximately 2-5% of the original amount of the liquid stabilising and/or blocking agent. This forms:
(a) a physical layer of stabiliser to form a protective shell over the bound biological material (such as antigen or antibody); and
(b) the liquid phase also ensures a wick effect is established between the surplus liquid around the beads and the partially liquid permeable surface.

The at least partially liquid permeable surface typically allows liquid to be drawn or wicked away. If insufficient liquid is present, excess liquid may not be wicked away and as the residual liquid around adjacent beads dries, they have been observed to stick together in clumps.

Typically, the at least partially liquid permeable surface is a paper or other fibrous type surface. The paper is typically of a size to allow the capacity of the paper to absorb the liquid.

Typically, the paper is filter paper, such as Code MN215, manufactured by Macherery-Nagel GmbH and Co. Such a paper has a relatively high flow rate (85 mm/10 mins) and a relatively smooth surface.

Typically such materials do not contain residual chemicals that could interfere with an immunoassay, specifically trace metal ions, enzymes, such as proteases or endonucleases, endotoxins, detergents, and azide.

Typical flow rates for the liquid permeable surface are 20 mm/10 minutes to 100 mm/10 minutes. The wicking effect of the surface draws liquid away so that stabilising chemicals when concentrated on drying, do not stick adjacent beads to one another.

Other materials may be used instead of paper.

Typically, the papers are cellulose based, such as wood pulp.

Typically, the beads are dried on the surface, for example under vacuum. Temperature utilised may be for example between −5° C. and 37° C., for example −5° C. to 30° C. and typically 0° C. to ambient temperature.

The Applicant has found that drying need not be under vacuum. Drying may be carried out under ambient pressure and for example ambient temperature (20° C.) to 37° C.

The dried beads may be removed from the surface. They may then be stored, for example, at −40° C. or 4° C. They may be stored, for example, in combination with a silica gel desiccant to remove moisture from the surrounding atmosphere and to maintain stability, and ideally in a hermetically sealed container.

The beads may also be dried by application of heat or at ambient temperature in a low humidity environment.

Liquid stabilising and/or blocking agent may be one or more compounds selected from sugars, polyols, surfactants, salts, polyethylene glycol (PEG), polymers, metal ions, proteins and amino acids. Such compounds are described generally in the articles by Wang, W[12,13]. Proteins are most typically used.

Other blocking materials include Block Ace™, a purified bovine milk protein (Snow Brand Milk Products Co. Ltd, Japan), glycerine, Lipidure™, a water soluble polymer of 2-methacryloyloxy ethyl phosphoryl choline, available from NOF Corporation, Japan (see Park, J-W[3]). Still other stabilising and/or blocking agents include mannitol, sucrose, trehalose, dextrose, sorbitol, cyclodextrin, hydroxyalkylcellulose and lactose. Preferably the stabilising and/or blocking agent is selected from Stabilcoat™ (a bovine protein containing formulation, typically diluted into a saline solution) and Stabilguard™ (a protein-free material, typically diluted into a saline solution), both of which are available from SurModics Inc, Eden Prairie, United States of America. Sucrose and lactose may also be utilised.

Typically a 50% v/v solution of Stabilcoat™ or Stabilguard™ is used.

Typically, the liquid stabiliser and/or blocking agent comprises BSA.

The beads may be polymeric or non-polymeric. The beads may be, for example, silica or most preferably polystyrene beads, they may be un-derivatised for passive absorption, or contain specific functional groups for covalent coupling, or specific linker proteins to bind the desired ligand. Such derivatising methods are generally known in the art. Typically the beads are 0.5 mm-5 mm in diameter, 1-3 mm, most typically 2 mm in diameter.

The beads may be polystyrene with surface functional groups such as carboxyl or amino groups for covalent coupling of proteins or other ligands.

The beads may be polystyrene with binding proteins such as Protein G, strepavidin or biotin for linking of proteins or other ligands.

The invention also provides beads obtainable by method of the invention.

A further aspect of the invention provides a plurality of beads coated with a biological material they comprise a stabiliser and/or blocking agent, characterised that the beads are not substantially aggregated. That is, the beads are substantially free-flowing and are not substantially attached to other beads.

The biological molecule, stabiliser and/or blocking agent and beads are typically as defined above.

A still further aspect of the invention provides a method of carrying out an immunoassay comprising providing a bead or a plurality of beads according to the invention.

An immunodiagnostic device comprising a bead or plurality of beads according to the invention also provided.

The invention will now be described by way of example only with reference to the following figures.

Figure 1:
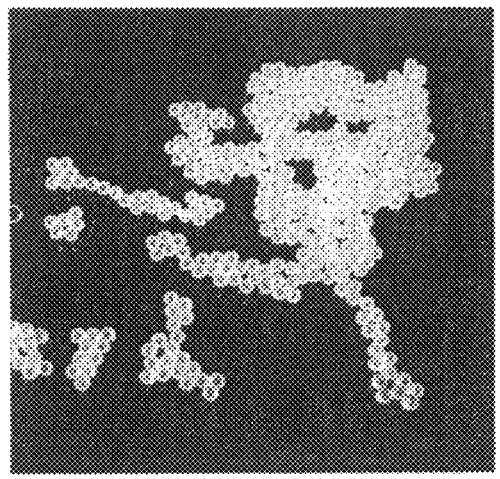
FIG. 1 shows beads dried in the polystyrene dish, these were observed to be clumped and to stick to the dish and adjacent beads.
Figure 2:
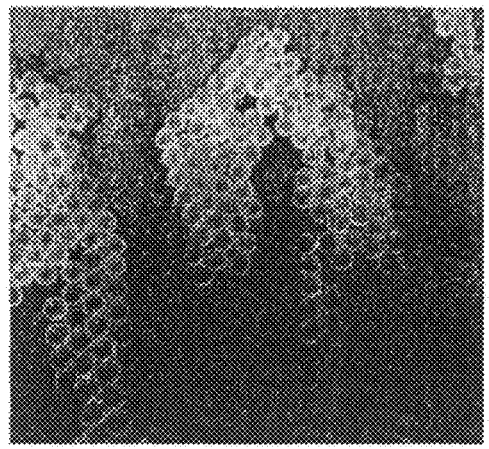
FIG. 2 shows beads dried on a siliconised paper, with the beads clumped and stuck to the paper and adjacent beads.
Figure 3:
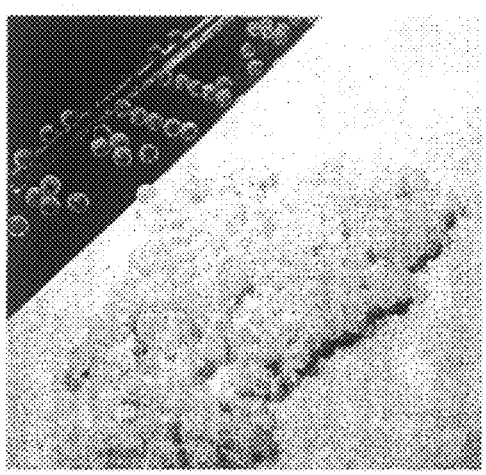
FIG. 3 shows beads dried on filter paper with the beads free and mobile.

The coating of the beads is conventional and generally known in the art. That is beads such as polystyrene beads were coated with an appropriate buffer, such as phosphate-buffered saline at pH 7.2 or carbonate pH 9.6, containing the required antigen or antibody at a typical concentration of between 0.5 and 20 ug/mL (depending on the protein) and gently mixed for 8-12 hours at room temperature. The volume of buffer equates to 504/bead, thus for 100,000 beads this equates to 5000 mL. Excess coat solution is then typically aspirated off. Next the blocking/stabilising buffer containing typically 50% Stabilcoat™ or Stabilguard™ was added and mixed at room temperature for 30 minutes, again using 504/bead. The majority of the residual blocking/stabilising buffer was then poured off. However, typically a small percentage of the liquid was retained, for example 2-5%. This was found to be necessary to allow a physical layer of stabiliser to form a protective shell over the bound antigen/antibody. The beads together with the remaining liquid were spread out onto the surface and then into shallow open trays where they were typically vacuum dried at ambient temperature. When the surface was a polystyrene dish, the beads were observed to clump and stick to the dish and adjacent beads (FIG. 1). Beads dried on siliconised paper which had a siliconised coating to repel moisture from the paper were observed to stick to the paper and adjacent beads (FIG. 2). However, beads dried on filter paper, which had some absorbency and allowed the liquid to wick away from the beads were found to be free and mobile (FIG. 3).

Typically, the beads were vacuum dried between 4-18 hours depending on the batch size. The dried beads were then poured into a suitable sized container for immediate use, or stored at −40° C. or 4° C. prior to insertion into for example, a microplate and sealed a foil pouch with a sachet of silica gel desiccant to minimise moisture ingression and maintain stability.

Alternative drying methods such as heat or ambient temperature in a low humidity environment also work but the drying time is extended.

REFERENCE

1. David Geoffrey Wild, The Immunoassay Handbook published by Elsevier ISBN: 0-08-044526-8 (2008)
2. John R. Crowther, The ELISA Theory and Practice. Humana Press ISBN:0-89603-279-5 (1995)
3. Park, J-W et al., Sensors and Actuators B, 91:158-162 (2003)
4. Engvall, E. And P. Perlmann, Immunochemistry, 8:871-873 (1971).
5. Sali, A. et al., Nature, 369:248-251 (1994)
6. Klotz, I., Archives Biochemistry & Biophysics, 116:92-96 (1966)
7. Asakura, T. et al., J. Bio Chem., 253:6423-6425 (1978)
8. Torchilin, V., Enzyme and Microbiological Technology, 1:74-82 (1979)
9. Maish, M., http:/www.sparknotes.com/health/aminoacids (2005)
10. Kanehisa, M. and T. Tsong, Biopolymers, 19:1617-1628 (1980)
11. Burley, S. and G. Petsko, Science, 229:23-28 (1985)
12. Wang, W., Intl. Jour. of Pharmaceutics, 185:129-188 (1999)
13. Wang, W., Intl. Jour. of Pharmaceutics, 289:1-30 (2005)
14. Lueng, W. et al., Jour. of Immunological Methods, 281:109-118 (2003).

What is claimed is:

1. A method of coating beads with a biological molecule comprising:
   (i) coating a plurality of beads with the biological molecule;
   (ii) mixing the coated beads with a liquid stabilising and/or blocking agent
   (iii) dispersing the coated beads still substantially surrounded by a liquid phase comprising the liquid stabilising and/or blocking agent across a surface that is at least partially liquid permeable;
   (iv) drying the beads on the surface to substantially remove the liquid phase, wherein the dried beads are free flowing; and
   (v) removing the dried beads from the surface.

2. A method according to claim 1, wherein the biological molecule is an antibody or fragment thereof capable of specifically binding an antigen, or an antibody.

3. A method according to claim 2, where the at least partially permeable surface is paper.

4. A method according to claim 3, wherein excess liquid stabilising and/or blocking agent is removed prior to dispersing the coated beads onto the at least partially liquid permeable surface.

5. A method according to claim 4, wherein the liquid stabilising and/or blocking agent comprises one or more compounds selected from sugars, polyols, surfactants, salts, polyethylene glycols (PEG), polymers, metal ions, proteins and amino acids.

6. A method according to claim 5, wherein the stabilising and/or blocking agent is selected from sucrose and lactose.

7. A method according to claim 5, wherein the beads are polystyrene beads 0.5 mm to 5 mm in diameter.

8. A method according to claim 7, wherein the polystyrene beads comprise carboxyl or amino groups for covalent coupling of proteins.

9. A method according to claim 4, wherein the liquid stabiliser and/or blocking agent comprises bovine serum albumin (BSA).

10. A method according to claim 7, wherein the polystyrene beads comprise Protein G, streptavidin or biotin for linking of proteins.

11. A method according to claim 4 wherein the beads in step (iv) are dried under vacuum at −5° C. to 37° C.

* * * * *